United States Patent [19]

Ohishi et al.

[11] Patent Number: 4,666,931
[45] Date of Patent: May 19, 1987

[54] BENZOFURAN DERIVATIVES USEFUL IN TREATING DIABETIC COMPLICATIONS

[75] Inventors: Yoshitaka Ohishi, Uji; Michiko Nagahara, Shiga; Norio Kajikawa, Kyoto; Motoyuki Yajima, Otsu; Katsumi Nogimori, Otsu; Shigeki Kurokawa, Otsu, all of Japan

[73] Assignee: Kaken Pharmaceutical Co., Ltd., Tokyo, Japan

[21] Appl. No.: 814,135

[22] Filed: Dec. 27, 1985

[30] Foreign Application Priority Data

Dec. 29, 1984 [JP] Japan ............................ 59-280801

[51] Int. Cl.$^4$ .................... A61K 31/34; C07D 307/80; C07D 307/82
[52] U.S. Cl. ................................ 514/389; 514/463; 514/469; 514/470; 548/309; 549/433; 549/466; 549/468; 549/470; 549/471
[58] Field of Search ............... 549/433, 466, 468, 470, 549/471; 548/309; 514/389, 463, 469, 470

[56] References Cited

U.S. PATENT DOCUMENTS 2,697,719 12/1954 Weisblat et al. .................. 562/430
4,540,704 9/1985 Ueda et al. ....................... 548/309
4,544,667 10/1985 Shepard et al. .................. 549/466

OTHER PUBLICATIONS

Aleksiev et al., Farmatsiya (Sofia) (1973), vol. 23(2), pp. 11-17, (Chemical Abstracts), vol. 79, 92556t, (1973).

Primary Examiner—John M. Ford
Assistant Examiner—Bernard I. Dentz
Attorney, Agent, or Firm—Armstrong, Nikaido, Marmelstein & Kubovcik

[57] ABSTRACT

A benzofuran derivative having the general formula (I):

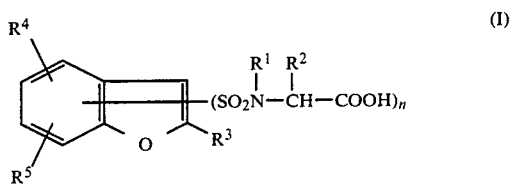

wherein $R^1$ is hydrogen atom, a benzyl group, unsubstituted or substituted with a halogen atom or an alkyloxy group, or an alkyl group having 1 to 3 carbon atoms, $R^2$ is hydrogen atom or an alkyl group having 1 to 3 carbon atoms, $R^3$ is acetyl group, ethyl group, carboxyl group or 4-methyl-2,5-dioxoimidazolidine-4-yl group, $R^4$ is hydrogen atom, hydroxyl group, an alkyl group having 1 to 6 carbon atoms, an alkoxy group having 1 to 9 carbon atoms, carboxymethoxy group, nitro group, acetoamino group, a benzylozy group unsubstituted or substituted with a halogen atom, nitro group or an alkyloxy group or a group having the formula: —$OR^6$, wherein $R^6$ is an alkenyl group having 2 to 4 carbon atoms or an alkyl group having 2 to 3 carbon atoms having a halogen atom, cyano group or oxo group, $R^5$ is hydrogen atom or methylenedioxy group together with $R^4$ group, n is 1 or 2, and the unsubstituted or substituted N-carboxymethylsulfamoyl group, $R^4$ and $R^5$ are attached at 3-position, 4-position, 5-position, 6-position or 7-position of the benzofuran ring, or a nontoxic salt thereof, process for preparing the same and a pharmaceutical composition containing the same.

The compounds of the present invention have powerful aldose reductase inhibiting activity, platelet aggregation inhibiting activity and arachidonic acid metabolism inhibiting activity and are useful for a remedy for treatment of diabetic complications.

25 Claims, No Drawings

BENZOFURAN DERIVATIVES USEFUL IN TREATING DIABETIC COMPLICATIONS

BACKGROUND OF THE INVENTION

The present invention relates to novel benzofuran derivatives, processes for preparing the same and a pharmaceutical composition, as a therapeutic agent for diabetic complications, containing the same.

In recent years, a marked increase in the number of diabetic patients needs urgently the treatment thereof.

As therapeutic agents for diabetes, insulin and blood sugar lowering agents have so far been used widely. However, diabetes is not a mere disorder of sugar metabolism but a disease also involving a variety of complications and therefore the therapeutic effects of the above-mentioned agents alone are not enough for the treatment of diabetes.

Main complications are neuropathy, cataract, nephritis and retinopathy and in the development of these complications as abnormal metabolism of polyols is concerned (K. H. Gabbay, Adv. Metab. Disord., 2 (2), 424 (1973)). That is, in the diabetic condition, polyols such as sorbitol are accumulated in the cell to an extraordinary extent, causing osmotic pressure increase and water swelling, which lead to cellular disturbance. Therefore, the above-mentioned diseases can be prevented and cured by inhibiting the aldose reductase activity which is essential to polyol synthesis (R. G. Judzewitsch et al., New Eng. J. Med., 308, 119 to 125 (1983); J. H. Kinoshita et al., Metabolism, 28 (1), 462 to 469 (1979)). In Japanese Unexamined Patent Publication Nos. 28074/1982 and 40478/1982, there is described aldose reductase inhibiting agents used as a remedy for diabetic complications.

In the complications such as cerebral and coronary vascular disturbances, accelerated platelet aggregation due to abnormal metabolism of arachidonic acid plays an important role for the development of the complications. That is, in the diabetic condition, the accelerated production of thromboxane $A_2$ results in the platelet aggregation to induce thrombosis, which leads to microangiopathy (Ryutaro Takahashi, Purosutaguranzin to Byotai, Gendaikagaku Zokan, P 112 to 120 (1984)). Among the complications, nephritis and retinopathy are typical microangiopathies. These complications can be prevented and treated by inhibiting the metabolism of arachidonic acid to improve the accelerated platelet aggregation in addition to inhibiting the accumulation of polyols.

SUMMARY OF THE INVENTION

It is an object of the present invention to provide a novel compound useful as a therapeutic agent for diabetic complications including perceptual disorder, autonomic disturbance, diabetic nephropathy, and ocular diseases such as retinopathy and catarct.

DETAILED DESCRIPTION

The present invention provides a benzofuran derivative having the general formula (I):

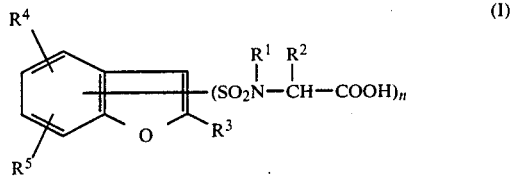

wherein $R^1$ is hydrogen atom, a benzyl group, unsubstituted or substituted with a halogen atom or an alkyloxy group, or an alkyl group having 1 to 3 carbon atoms, $R^2$ is hydrogen atom or an alkyl group having 1 to 3 carbon atoms, $R^3$ is acetyl group, ethyl group, carboxyl group or 4-methyl-2,5-dioxoimidazolidine-4-yl group, $R^4$ is hydrogen atom, hydroxyl group, an alkyl group having 1 to 6 carbon atoms, an alkoxy group having 1 to 9 carbon atoms, carboxymethoxy group, nitro group, acetoamino group, a benzyloxy group unsubstituted or substituted with a halogen atom, nitro group or an alkyloxy group or a group having the formula: $-OR^6$, wherein $R^6$ is an alkenyl group having 2 to 4 carbon atoms or an alkyl group having 2 to 3 carbon atoms having a halogen atom, cyano group or oxo group, $R^5$ is hydrogen atom or methylenedioxy group together with $R^4$ group, n is 1 or 2, and the unsubstituted or substituted N-carboxymethylsulfamoyl group, $R^4$ and $R^5$ are attached at 3-position, 4-position, 5-position, 6-position or 7-position of the benzofuran ring, or a nontoxic salt thereof and a process for preparing the same.

The benzofuran derivatives having the general formula (I) of the present invention are prepared by reacting the compound having the general formula (II):

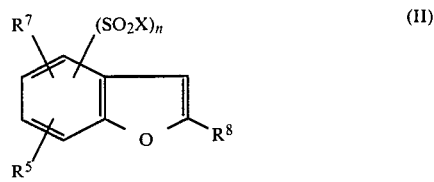

wherein X is a halogen atom, $R^5$ is hydrogen atom or methylenedioxy group together with $R^6$ group, $R^7$ is hydrogen atom, an alkyl group having 1 to 6 carbon atoms, an alkoxy group having 1 to 9 carbon atoms, an alkoxycarbonylmethoxy group having 1 to 6 carbon atoms, nitro group, acetoamino group, benzyloxy group, unsustituted or substituted with a halogen atom, nitro group or an alkyloxy group, an alkenyloxy group having 2 to 4 carbon atoms, or an alkoxy group having 2 to 3 carbon atoms having a halogen atom, cyano group or oxo group, $R^8$ is acetyl group, ethyl group, an alkoxycarbonyl group, an alkoxycarbonylmethoxycarbonyl group having 1 to 3 carbon atoms, cyano group or 4-methyl-2,5-dioxoimidazolidine-4-yl group and n is 1 or 2, with amine compound having the general formula (III):

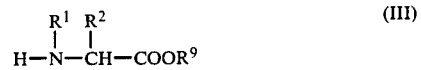

wherein $R^1$ is hydrogen atom, a benzyl group, unsubstituted or substituted with a halogen atom or an alkyloxy group, or an alkyl group having 1 to 3 carbon atoms, $R^2$ is hydrogen atom or alkyl group having 1 to 3 carbon atoms and then either hydrolyzing the obtained ester or simultaneously conducting the hydrolysis and the ether bond-cleavage of the ester, thereby the compound having the general formula (II) can be obtained by reacting the benzofuran derivatives having the general formula (II'):

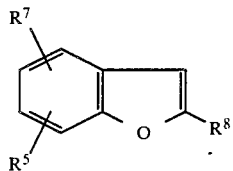

wherein $R^5$, $R^7$ and $R^8$ are as above, with $ClSO_3H$.

When the compound having the general formula (II') is reacted with $ClSO_3H$, either a solution of the compound having the general formula (II') dissolved in an aprotic solvent such as chloroform, carbon tetrachloride, dichloromethane or dichloroethane, or the compound having the general formula (II') is added to 5 or 20 times the amount of $clSO_3H$ at $-20°$ to $10°$ C. and the mixture is further stirred at $-20°$ to $25°$ C. to complete the reaction. The resultant is then poured into ice-water to form precipitate, which is filtered or extracted with a solvent such as ethylacetate to give a chlorosulfonyl compound having the general formula (II). The chlorosulfonyl compound is added to an aprotic solvent such as chloroform, dichloromethane, dichloroethane or carbon tetrachloride, to which 1 to 2.5 molar equivalents of the amine having the general formula (III) and 1 to 2.5 molar equivalents of organic amine such as diethylamine or triethylamine are added dropwise. After the mixture is stirred at $20°$ to $50°$ C. for 3 to 24 hours and poured into water, the resultant is extracted with a solvent such as ethylacetate or ether and the solvent is distilled away to give an ester compound, which is recrystallized from ethylacetate, ethanol, a mixture of ethylacetate and ethanol, a mixture of ethylacetate and petroleum benzin or a mixture of ethanol and water. The ester compound is hydrolyzed by stirring at $10°$ to $50°$ C. for 1 to 5 hours either in an aqueous alkaline solution of sodium hydroxide, potassium hydroxide or the like, or in the aqueous alkaline solution in a solvent such as methanol, ethanol or dimethylsulfoxide, or by reacting in trifluoroacetic acid at $20°$ to $30°$ C. for 1 to 3 hours.

The crude crystalline material, which is obtained by acidifying the reaction solution when the hydrolysis is carried out with alkali or obtained by distilling away trifluoroacetic acid when the hydrolysis is carried out with trifluoroacetic acid, is recrystallized from ethanol, methanol, a mixture of ethanol and water, a mixture of dimethylsulfoxide and water, and the like to give the benzofuran derivatives having the general formula (I). Alternatively, a mixture of the ester compound and 2.5 molar equivalent of $AlCl_3$ is stirred in a solvent such as chlorobenzene or nitrobenzene at $100°$ to $120°$ C. for 1 to 7 hours and the resultant is poured into an aqueous solution of hydrochloric acid to simultaneously carry out the hydrolysis and the cleavage of the ester, the obtained crude crystal being recrystallized from ethanol, methanol, water or dimethylsulfoxide to give the benzofuran derivatives having the general formula (I).

Examples of the nontoxic salts of the benzofuran derivatives having the general formula (I) are pharmaceutically acceptable salts such as sodium salt, potassium salt, magnesium salt, calcium salt and salts with organic amine compounds.

The following Table 1 shows typical compounds of the benzofuran derivatives having the general formula (I) of the present invention.

TABLE 1

| Compound No. | Structural formula | Compound name |
|---|---|---|
| 1 | A, CH₃O, COCH₃ structure | 2-Acetyl-4-(N—carboxymethylsulfamoyl)-7-methoxybenzofuran |
| 2 | A, C₂H₅O, COCH₃ structure | 2-Acetyl-4-(N—carboxymethylsulfamoyl)-7-ethoxybenzofuran |
| 3 | A, CH₃(CH₂)₂O, COCH₃ structure | 2-Acetyl-4-(N—carboxymethylsulfamoyl)-7-n-propoxybenzofuran |

TABLE 1-continued

| Compound No. | Structural formula | Compound name |
|---|---|---|
| 4 | 4-A, 7-OCH$_2$CH$_2$CH$_2$CH$_3$, 2-COCH$_3$ benzofuran | 2-Acetyl-4-(N—carboxymethylsulfamoyl)-7-n-butoxybenzofuran |
| 5 | 4-A, 7-O(CH$_2$)$_4$CH$_3$, 2-COCH$_3$ benzofuran | 2-Acetyl-4-(N—carboxymethylsulfamoyl)-7-n-pentyloxybenzofuran |
| 6 | 4-A, 7-O(CH$_2$)$_5$CH$_3$, 2-COCH$_3$ benzofuran | 2-Acetyl-4-(N—carboxymethylsulfamoyl)-7-n-hexyloxybenzofuran |
| 7 | 4-A, 7-O(CH$_2$)$_6$CH$_3$, 2-COCH$_3$ benzofuran | 2-Acetyl-4-(N—carboxymethylsulfamoyl)-7-n-heptyloxybenzofuran |
| 8 | 4-A, 7-OCH$_2$COOH, 2-COCH$_3$ benzofuran | 2-Acetyl-4-(N—carboxymethylsulfamoyl)-7-carboxymethoxybenzofuran |
| 9 | 4-SO$_2$N(CH$_3$)CH$_2$COOH, 7-O(CH$_2$)$_3$CH$_3$, 2-COCH$_3$ benzofuran | 2-Acetyl-4-(N—methyl-N—carboxymethylsulfamoyl)7-n-butoxybenzofuran |
| 10 | 4-SO$_2$N(CH$_3$)—CH(CH$_3$)COOH, 7-O(CH$_2$)$_3$CH$_3$, 2-COCH$_3$ benzofuran | 2-Acetyl-4-[N—methyl-N—(1-carboxyethylsulfamoyl)]-7-n-butoxybenzofuran |
| 11 | 4-SO$_2$NHCH(CH$_3$)COOH, 7-O(CH$_2$)$_3$CH$_3$, 2-COCH$_3$ benzofuran | 2-Acetyl-4-[N—(1-carboxyethyl)sulfamoyl)]-7-n-butoxybenzofuran |

TABLE 1-continued

| Compound No. | Structural formula | Compound name |
|---|---|---|
| 12 | (benzofuran with A at 4-position, OCH₂COOH at 7-position, COOH at 2-position) | 2-Caboxy-4-(N—carboxymethylsulfamoyl)-7-carboxymethoxybenzofuran |
| 13 | (benzofuran with A at 4-position, CH₃O at 7-position, COOH at 2-position) | 2-Acetyl-4-(N—carboxymethylsulfamoyl)-7-methoxybenzofuran |
| 14 | (benzofuran with A at 4-position, C₂H₅O at 7-position, COOH at 2-position) | 2-Acetyl-4-(N—carboxymethylsulfamoyl)-7-ethoxybenzofuran |
| 15 | (benzofuran with A at 4-position, CH₃ at 7-position, COCH₃ at 2-position) | 2-Acetyl-4-(N—carboxymethylsulfamoyl)-7-methylbenzofuran |
| 16 | (benzofuran with A at 4-position, CH₃CH₂CH(CH₃)— at 7-position, COCH₃ at 2-position) | 2-Acetyl-4-(N—carboxymethylsulfamoyl)-7-sec-butylbenzofuran |
| 17 | (benzofuran with A at 4-position, 5,6-methylenedioxy, COCH₃ at 2-position) | 2-Acetyl-4-(N—carboxymethylfulfamoyl)-5,6-methylenedioxybenzofuran |
| 18 | (benzofuran with OCH₃ at 4-position, A at 7-position, COCH₃ at 2-position) | 2-Acetyl-4-methoxy-7-(N—carboxymethylsulfamoyl)benzofuran |
| 19 | (benzofuran with A at 4-position, CH₃O at 7-position, 4-methyl-2,5-dioxoimidazolidine-4-yl at 2-position) | 2-(4-methyl-2,5-dioxoimidazolidine-4-yl)-4-(N—carboxymethylsulfamoyl)-7-methoxybenzofuran |

TABLE 1-continued

| Compound No. | Structural formula | Compound name |
|---|---|---|
| 20 | | 2-(4-methyl-2,5-dioxo-imidazolidine-4-yl)-4,6-di(N—carboxymethyl)-sulfamoyl)-7-methoxy-benzofuran |
| 21 | | 2-Ethyl-3-(N—carboxy-methylsulfamoyl)-5-nitrobenzofuran |
| 22 | | 2-Ethyl-3-(N—carboxy-methylsulfamoyl)-5-acetylaminobenzofuran |
| 23 | | 2-Acetyl-4-(N—carboxy-methylsulfamoyl)-7-p-nitrobenzyloxybenzofuran |
| 24 | | 2-Acetyl-4-(N—carboxy-methylsulfamoyl)-7-p-methoxybenzyloxy-benzofuran |
| 25 | | 2-Acetyl-4-(N—carboxy-methylsulfamoyl)-7-(2-chloropropyloxy)-benzofuran |
| 26 | | 2-Acetyl-4-(N—carboxy-methylsulfamoyl)-7-acetonyloxybenzofuran |
| 27 | | 2-Acetyl-4-(N—carboxy-methylsulfamoyl)-7-cyanomethyloxybenzofuran |

TABLE 1-continued

| Compound No. | Structural formula | Compound name |
|---|---|---|
| 28 | 4-A, 7-OH benzofuran-2-COCH₃ | 2-Acetyl-4-(N—carboxymethylsulfamoyl)-7-hydroxybenzofuran |
| 29 | 4-A, 7-OCH₂C₆H₅ benzofuran-2-COCH₃ | 2-Acetyl-4-(N—carboxymethylsulfamoyl)-7-benzyloxybenzofuran |
| 30 | 4-A, 7-OCH₂-C₆H₄-Cl benzofuran-2-COCH₃ | 2-Acetyl-(N—carboxymethylsulfamoyl)-7-p chlorobenzyloxybenzofuran |
| 31 | 4-A, 7-OCH₂CH=CH₂ benzofuran-2-COCH₃ | 2-Acetyl-4-(N—carboxymethylsulfamoyl)-7-allyloxybenzofuran |
| 32 | 4-A, 7-OCH₂CH₂CH=CH₂ benzofuran-2-COCH₃ | 2-Acetyl-4-(N—carboxymethylsulfamoyl)-7-(3-butenyloxy)benzofuran |
| 33 | 4-SO₂N(CH₂C₆H₄-OCH₃)CH₂COOH, 7-OCH₂-C₆H₄-OCH₃ benzofuran-2-COCH₃ | 2-Acetyl-4-(N—p-methoxybenzyl-N—carboxymethylsulfamoyl)-7-p-methoxybenzyloxybenzofuran |

TABLE 1-continued

| Compound No. | Structural formula | Compound name |
|---|---|---|
| 34 | 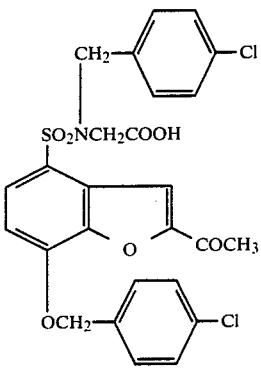 | 2-Acetyl-4-(N—p-chlorobenzyl-N—carboxymethylsulfamoyl)-7-p-chlorobenzyloxybenzofuran |
| 35 | 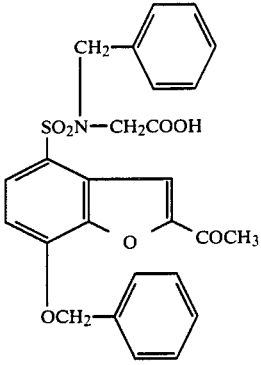 | 2-Acetyl-4-(N—benzyl-N—carboxymethylfulfamoyl)-7-benzyloxybenzofuran |

(Note)
A: $SO_2NHCH_2COOH$

Pharmacological activities of the compound having the general formula (I) of the present invention are provided by the following detailed explanation.

[ALDOSE REDUCTASE INHIBITING ACTIVITY]

The compound having the general formula (I) of the present invention shows aldose reductase inhibiting activity and is useful for the prevention and treatment of neuropathy, diabetic retinopathy and cataract resulting from abnormal accumulation of polyols. For example, in the experiment in a laboratory, all the compounds of the present invention showed 50% inhibition against the activity of aldose reductase from rat lens in a concentration of from $10^{-8}$ to $10^{-6}$M, which are presented in Table 2.

TEST METHOD

The test was carried out according to the method of Hayman et al. (S. Hyman and J. H. Kinoshita, J. Biol, Chem., 240, 877 to 882 (1965)).

Wistar male rats were sacrificed by decapitation and the lenses were taken out to be homogenized with a 0.1M phosphate buffer [pH 6.8, containing 1 mM of mercaptoethanol and 1 mM of nicotinamide-adenine dinucleotide phosphate (NADP)]. The homogenate was then centrifuged at 10,000 g for 15 minutes and the supernatant was prepared as the crude enzyme solution.

Separately, a 0.1M phosphate buffer (pH 6.2) containing 0.104 mM of NADPH (reduced form of NADP) and 10 mM of DL-glyceraldehyde was prepared, to which 15 μl of each solution of test compound in varied concentrations was added, followed by addition of 25 μl of the crude enzyme solution previously prepared, thereby initiating the reaction. The decrease in absorbance at 340 nm was measured using a high-sensitivity self-registering spectrophotometer (Model SM-401 made by Union Giken Kabushiki Kaisha).

The results are shown in Table 2 in term of $IC_{50}$ (50% inhibition concentration in M).

TABLE 2

| Compound No. | $IC_{50}(M)$ |
|---|---|
| 1 | $2 \times 10^{-7}$ |
| 2 | $1 \times 10^{-7}$ |
| 3 | $6 \times 10^{-8}$ |
| 4 | $4 \times 10^{-8}$ |
| 5 | $5 \times 10^{-8}$ |
| 6 | $5 \times 10^{-8}$ |
| 7 | $3 \times 10^{-8}$ |
| 8 | $2 \times 10^{-7}$ |
| 9 | $1 \times 10^{-6}$ |
| 10 | $7 \times 10^{-6}$ |
| 11 | $5 \times 10^{-6}$ |
| 12 | $2 \times 10^{-7}$ |
| 13 | $1 \times 10^{-7}$ |
| 14 | $7 \times 10^{-8}$ |
| 15 | $5 \times 10^{-7}$ |
| 16 | $4 \times 10^{-7}$ |
| 17 | $2 \times 10^{-6}$ |
| 18 | $5 \times 10^{-6}$ |
| 19 | $2 \times 10^{-6}$ |
| 20 | $3 \times 10^{-7}$ |
| 21 | $5 \times 10^{-8}$ |
| 22 | $5 \times 10^{-8}$ |
| 23 | $5 \times 10^{-8}$ |
| 24 | $3 \times 10^{-8}$ |
| 25 | $2 \times 10^{-7}$ |
| 26 | $2 \times 10^{-7}$ |

TABLE 2-continued

| Compound No. | IC$_{50}$(M) |
| --- | --- |
| 27 | $1 \times 10^{-7}$ |
| 28 | $8 \times 10^{-8}$ |
| 29 | $5 \times 10^{-8}$ |
| 30 | $4 \times 10^{-8}$ |
| 31 | $5 \times 10^{-8}$ |
| 32 | $3 \times 10^{-8}$ |
| 33 | $8 \times 10^{-7}$ |
| 34 | $8 \times 10^{-7}$ |
| 35 | $7 \times 10^{-7}$ |
| Sorbinil (Note) | $2 \times 10^{-7}$ |

Note:
USAN (United States Adopted Names) of S—6-fluoro-spiro(chroman-4,4'-imidazolidine-2',5'-dione having the following formula:

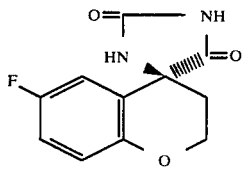

[PLATELET AGGREGATION INHIBITING ACTIVITY]

The benzofuran derivatives having the general formula (I) of the present invention show platelet aggregation inhibiting activity and are useful for the prevention and treatment of diabetic complication such as cardiovascular disease. In the experiment in a laboratory, the benzofuran derivatives of the compound Nos. 5, 8, 9, 10, 11, 23, 29, 30 and 33 showed 50% inhibition against the aggregation of the washed rabbit platelet by thrombin in a concentration of from $2 \times 10^{-5}$ to $2 \times 10^{-4}$M. The compounds of the present invention other than the above-mentioned compounds also showed platelet aggregation inhibiting activity, though the activity is somewhat lower than that of the above nine compounds which showed the activity equivalent to or more than that of the widely used platelet aggregation inhibiting agents, Persntin ® (the registered trademark of dipyridamole made by Tanabe Seiyaku CO., LTD.).

TEST METHOD

Blood samples were collected from the auricular blood vessel of rabbits (white local breed), and washed platelets were prepared therefrom by the method of Baenziger et al. (N. L. Baenziger and P. W. Majerus, Methods Enzymol., 31, 149 to 155 (1974). The platelets were suspended in a 15 mM Tris-hydrochloric acid buffer with a final concentration of $6 \times 10^8$ cells/ml (Tris: tris(hydroxymethyl)aminomethane). Each test compound of the compound Nos. 5, 8, 9, 11, 23, 29, 30 and 33 and Persantin ® was added thereto and incubation was carried out at 37° C. for 2 minutes. Then the platelets were stimulated by addition of thrombin (0.2 unit/ml of final concentration; made by Mochida Pharmaceutical Co.) and the aggregation inhibiting activity was estimated by the observation of the aggregation reaction using an aggregometer (made by Briston Co.).

The results are shown in Table 3 in terms of IC$_{50}$ (50% inhibiton concentration in M).

TABLE 3

| Compound No. | IC$_{50}$ (M) |
| --- | --- |
| 7 | $1.5 \times 10^{-4}$ |
| 8 | $1.3 \times 10^{-4}$ |
| 9 | $6.0 \times 10^{-4}$ |
| 10 | $1.6 \times 10^{-4}$ |

TABLE 3-continued

| Compound No. | IC$_{50}$ (M) |
| --- | --- |
| 11 | $1.6 \times 10^{-4}$ |
| 23 | $8.0 \times 10^{-5}$ |
| 29 | $3.5 \times 10^{-5}$ |
| 30 | $3.0 \times 10^{-5}$ |
| 33 | $2.0 \times 10^{-5}$ |
| Persantin ® | $2.0 \times 10^{-4}$ |

[ACUTE TOXICITY]

Acute toxicity test in mice was carried out on the benzofuran derivatives of the compound Nos. 3, 5, 9, 21, 23, 26, 29 and 34. The benzofuran derivatives of the compound Nos. 3, 5, 9 and 21 induced no death up to the dose of 3 g/kg body weight and had the LD$_{50}$ value (oral) of more than 3 g/kg body weight while the benzofuran derivatives of the compound Nos. 23, 26, 29 and 34 induced no death up to 2 g/kg body weight and had the LD$_{50}$ value (oral) of more than 2 g/kg body weight. This fact shows that the benzofuran derivatives of the present invention have quite low toxicity.

TEST METHOD

To groups of 4 male ddY mice (5 weeks of age) were orally administered by gavage each test compound (2, 3 and 4 g/kg body weight with respect to the compound Nos. 3, 5, 9 and 21, 1, 2 and 3 g/kg body weight with respect to the compound Nos. 23, 26, 29 and 34) suspended in a 10% gum arabic and the mice were observed for death or survival for 2 weeks.

[ARACHIDONIC ACID METABOLISM INHIBITING ACTIVITY]

The benzofuran derivatives of the compound Nos. 8, 13, 14, 19, 20, 23, 29, 30 and 33 show arachidonic acid metabolism inhibiting activity; i.e. they showed 50% inhibition against the production of malondialdehyde from arachidonic acid by rabbit platelets in a concentration of $10^{-5}$ to $10^{-4}$M, which exhibits that the above compounds have an activity 2 to 11 times stronger than that of the powerful cyclooxygenase inhibitor, indomethancin. Also in the experiment using 9000 G supernatant of lung homogenate taken from guinea pig, the above compounds showed an inhibition against the production of malonedialdehyde from arachidonic acid with an activity equivalent to or more than that of aspirin.

TEST METHOD

Washed rabbit platelets prepared as in the platelet aggregation inhibiting activity test were suspended in 15 mM Tris-hydrochloric acid buffer with a final concentration of $1 \times 10^8$ cell/ml, to which each test compound of the compound Nos. 8, 13, 14, 19, 20, 23, 29, 30 and 33 were added and the resultant was preincubated at 37° C. for five minutes. Then arachidonic acid (a final concentration: 0.2 mM, made by Sigma Chemical Co.) was added thereto and the mixture was preincubated for 1 minute. An amount of the produced malondialdehyde was measured according to the thiobarbiturates method (Ed. Aoki and Shibata, Ketsuekigaku Kenkyukensaho, P 441 to 447).

Lung from guinea pig was washed with physiological saline and homogenized in 0.1M Tris-hydrochloric acid buffer to prepare a supernatant by cooled centrifugation (9000 G).

The inhibiting activity against cyclooxygenase was measured by using the 9000 G supernatant as a source of cyclooxygenase in the presence of 1 mM epinephiline.

The compounds of the present invention have powerful aldose reductase inhibiting activity, platelet aggregation inhibiting activity and arachidonic acid metabolism inhibiting activity and are useful for a remedy for treatment of diabetic complications.

The compounds of the present invention can be formulated into pharmaceutical compositions in the form of tablets, capsules, injections, pills, granules, suppositories and eye drops. The pharmaceutical compositions of the present invention are administered with an effective dose of around 50 to around 500 mg/day for adults.

The present invention is more specifically described and explained by the following Examples. However, it is to be understood that the present invention is not limited to the Examples, and various changes and modifications can be made without departing from the spirit and scope of the present invention.

EXAMPLE 1

[Preparation of 2-acetyl-4(N-carboxymethylsulfamoyl)-7-methoxybenzofuran (Compound No. 1)]

2-Acetyl-7-methoxybenzofuran (5 g) (0.0263 mole) was added to chlorosulfonic acid (18.4 g) (0.158 mole) at $-15°$ C. in portionwise (each 0.5 g) for 30 min. After stirring the reaction mixture at $-10°$ to $-5°$ C. for 1 hour, the resultant was gradually added dropwise to ice. The solution was extracted with ethyl acetate, washed with water and dried, followed by distilling away ethyl acetate under reduced pressure to give 5.8 g of crude 2-acetyl-4-chlorosulfonyl-7-methoxybenzofuran.

Yield: 77%.

Mass Spectrum (m/z): 288 (M+), 274, 253 and 239.

A mixture of the chlorosulfonyl compound (1.5 g) (5.2 mmol), glycine ethyl ester hydrochloride (0.87 g) (6.24 mmol) and triethylamine (0.63 g) (6.24 mmole) in dichloromethane (15 ml) was stirred at 25° to 35° C. for 5 hours. Then the reaction mixture was filtered and filtrate was distilled away, the residue being extracted with ethyl acetate. The ethyl acetate layer was washed with water and dried and ethyl acetate was distilled away under reduced pressure to give a white powder, which was recrystallized with ethanolacetone (1:1) to give 1.2 g of 2-acetyl-4-(N-ethoxycarboxymethylsulfamoyl)-7-methoxybenzofuran (hereinafter referred to as "ester compound").

yield: 65%.

Mass Spectrum (m/z): 355 (M+), 282 and 253.

2N-NaOH aqueous solution (0.3 ml) (1.0 mmole) was added to the ester compound (0.3 g) (0.845 mmole) in methanol (10 ml) and the mixture was stirred at 25° to 30° C. for 1 hour, followed by adjusting the reaction mixture to pH 2 with 2N-HCl to give a white powder, which was recrystallized with methanol to give 0.23 g of 2-acetyl-4-(N-carboxymethylsulfamoyl)-7-methoxybenzofuran as white prism crystals (yield: 83%).

The physical constants such as melting point (MP), proton nuclear magnetic resonance ($^1$H-NMR), elementary analysis (EA) and mass spectrum (MS) are shown in Table 4.

EXAMPLE 2

[Preparation of 2-acetyl-4-(N-carboxymethylsulfamoyl)-7-ethoxybenzofuran (Compound No. 2)]

2-Acetyl-7-ethoxybenzofuran obtained by the reaction of 2-acetyl-7-hydroxybenzofuran and ethyl iodide (yield: 87%, MS (m/z): 204 (M+), 176 and 161 was reacted with chlorosulfonic acid as in Example 1 to yield a chlorosulfonyl compound (yield: 90%, MS (m/z): 302 (M+), 274 and 239). The obtained chlorosulfonyl compound was reacted with glycine ethyl ester hydrochloride to give an ester compound (yield: 73%, MS (m/z): 369 (M+), 296, 267, and 239), which was then hydrolyzed to give 2-acetyl-4-(N-carboxymethylsulfamoyl)-7-ethoxybenzofuran (white prisms, yield: 81%). The physical constants are shown in Table 4.

EXAMPLE 3

[Preparation of 2-acetyl-4-(N-carboxymethylsulfamoyl)-7-n-propoxybenzofuran (Compound No. 3)]

2-Acetyl-7-n-propoxybenzofuran obtained by the reaction of 2-acetyl-7-hydroxybenzofuran and n-propyl iodide (yield: 78%, MS (m/z): 218 (M+), 176 and 161) was reacted with chlorosulfonic acid as in Example 1 to yield a chlorosulfonyl compound (yield: 45%, MS (m/z): 316 (M+), 281, 274 and 239). The obtained chlorosulfonyl compound was reacted with glycine ethyl ester hydrochloride to give an ester compound (yield: 99%, MS (m/z): 383 (M+), 341, 281 and 239), which was then hydrolyzed to give 2-acetyl-4-(N-carboxymethylsulfamoyl)-7-n-propoxybenzofuran (white prisms, yield: 74%). The physical constants are shown in Table 4.

EXAMPLE 4

[Preparation of 2-acetyl-4-(N-carboxymethylsulfamoyl)-7-n-butoxybenzofuran (Compound No. 4)]

2-Acetyl-7-n-butoxybenzofuran obtained by the reaction of 2-acetyl-7-hydroxybenzofuran and n-butyl iodide (yield: 98%, MS (m/z): 232 (M+), 176 and 161) was reacted with chlorosulfonic acid as in Example 1 to yield a chlorosulfonyl compound (yield: 78%, MS (m/z): 330 (M+), 295, 274 and 239). The obtained chlorosulfonyl compound was reacted with glycine ethyl ester hydrochloride to give an ester compound (yield: 92%, MS (m/z): 397 (M+), 341, 295 and 239), which was then hydrolyzed to give 2-acetyl-4-(N-carboxymethylsulfamoyl)-7-n-butoxybenzofuran (white prisms, yield: 81%). The physical constants are shown in Table 4.

EXAMPLE 5

[Preparation of 2-acetyl-4-(N-carboxymethylsulfamoyl)-7-n-pentyloxybenzofuran (Compound No. 5)]

2-Acetyl-7-n-pentyloxybenzofuran obtained by the reaction of 2-acetyl-7-hydroxybenzofuran and n-pentyl iodide (yield: 90%, MS (m/z): 246 (M+), 176 and 161) was reacted with chlorosulfonic acid as in Example 1 to yield a chlorosulfonyl compound (yield: 52%, MS (m/z): 344 (M+), 309, 274 and 239). The obtained chlorosulfonyl compound was reacted with glycine ethyl ester hydrochloride to give an ester compound (yield:

85%, MS (m/z): 411 (M+), 341, 309, 268 and 239), which was then hydrolyzed to give 2-acetyl-4-(N-carboxymethylsulfamoyl)-7-n-pentyloxybenzofuran (light yellow prisms, yield: 63%). The physical constants are shown in Table 4.

EXAMPLE 6

[Preparation of 2-acetyl-4-(N-carboxymethylsulfamoyl)-7-n-hexyloxybenzofuran (Compound No. 6)]

2-Acetyl-7-n-hexyloxybenzofuran obtained by the reaction of 2-acetyl-7-hydroxybenzofuran and n-hexyl iodide (yield: 87%, MS (m/z): 260 (M+), 176 and 161) was reacted with chlorosulfonic acid as in Example 1 to yield a chlorosulfonyl compound (yield: 43%, MS (m/z): 358 (M+), 274 and 239). The obtained chlorosulfonyl compound was reacted with glycine ethyl ester hydrochloride to give an ester compound (yield: 76%, MS (m/z): 425 (M+), 341, 268 and 239), which was then hydrolyzed to give 2-acetyl-4-(N-carboxymethylsulfamoyl)-7-n-hexyloxybenzofuran (light yellow prisms, yield: 83%). The physical constants are shown in Table 4.

EXAMPLE 7

[Preparation of 2-acetyl-4-(N-carboxymethylsulfamoyl)-7-n-heptyloxybenzofuran (Compound No. 7)]

2-Acetyl-7-n-heptyloxy-benzofuran obtained by the reaction of 2-acetyl-7-hydroxybenzofuran and n-heptyl iodide (yield: 89%, MS (m/z): 274 (M+), 176 and 161) was reacted with chlorosulfonic acid as in Example 1 to yield a chlorosulfonyl compound (yield: 39%, MS (m/z): 372 (M+), 274 and 239). The obtained chlorosulfonyl compound was reacted with glycine ethyl ester hydrochloride to give an ester compound (yield: 91%, MS (m/z): 411 (M+), 314 and 239), which was then hydrolyzed to give 2-acetyl-4-(N-carboxymethylsulfamoyl)-7-n-heptyloxybenzofuran (light yellow prisms, yield: 92%). The physical constants are shown in Table 4.

EXAMPLE 8

[Preparation of 2-acetyl-4-(N-carboxymethylsulfamoyl)-7-(carboxymethoxy)benzofuran (Compound No. 8)]

2-Acetyl-7-(ethoxycarbonylmethoxy)benzofuran obtained by the reaction of 2-acetyl-7-hydroxybenzofuran and ethyl bromoacetate (yield: 76%, MS (m/z): 262 (M+), 247 and 189) was reacted with chlorosulfonic acid as in Example 1 to yield a chlorosulfonyl compound (yield: 73%, MS (m/z): 360 (M+), 325 and 287). The obtained chlorosulfonyl compound was reacted with glycine ethyl ester hydrochloride to give an ester compound (yield: 85%, MS (m/z): 427 (M+), 354, 325 and 261), which was then hydrolyzed to give 2-acetyl-4-(N-carboxymethylsulfamoyl)-7-(carboxymethoxy)benzofuran (colorless plates, yield: 91%). The physical constants are shown in Table 3.

EXAMPLE 9

[Preparation of 2-acetyl-4-(N-methyl-N-carboxymethylsulfamoyl)-7-n-butoxybenzofuran (Compound No. 9)]

The procedures of Example 4 were repeated except that sarcosine methyl ester hydrochloride was reacted in place of glycine ethyl ester hydrochloride to give an ester compound (yield: 49%, MS (m/z): 397 (M+), 338, 295 and 239), which was then hydrolyzed to give 2-acetyl-4-(N-methyl-N-carboxymethylsulfamoyl)-7-n-butoxybenzofuran (yellow plates: yield: 65%). The physical constants are shown in Table 4.

EXAMPLE 10

[Preparation of 2-acetyl-4-(N-methyl-N-(1-carboxyethyl)sulfamoyl]-7-n-butoxybenzofuran (Compound No. 10)]

The procedures of Example 4 were repeated except that N-methyl-L-alanine methyl ester hydrochloride was reacted instead of glycine ethyl ester hydrochloride to give an ester compound (yield: 62%, MS (m/z): 411 (M+), 352, 295 and 239), which was then hydrolyzed to give 2-acetyl-4-(N-methyl-N-(1-carboxyethyl)sulfamoyl)-7-n-butoxybenzofuran (yellow prisms: yield: 84%). The physical constants are shown in Table 4.

EXAMPLE 11

[Preparation of 2-acetyl-4-(N-(1-carboxyethyl)sulfamoyl)-7-n-butoxybenzofuran (Compound No. 11)]

The procedure of Example 4 were repeated except that L-alanine ethyl ester hydrochloride was reacted in place of glycine ethyl ester hydrochloride to give an ester compound (yield: 48%, MS (m/z): 411 (M+), 338, 295 and 239), which was then hydrolyzed to give 2-acetyl-4-(N-(1-carboxyethyl)sulfamoyl)-7-n-butoxybenzofuran (light yellow prisms: yield: 92%). The physical constants are shown in Table 4.

EXAMPLE 12

[Preparation of 2-carboxy-4-(N-carboxymethylsulfamoyl)-7-(carboxymethoxy)benzofuran (Compound No. 12)]

2-Carboxy-7-hydroxybenzofuran and ethyl bromoacetate were reacted to give 2-(ethoxycarbonylmethoxycarbonyl)-7-(ethoxycarbonylmethoxy)benzofuran (yield: 78%, MS (m/z): 350 (M+), 305, 277, 249 and 219), which was then reacted with chlorosulfonic acid as in Example 1, yielding 2-(ethoxycarbonylmethoxycarbonyl)-4-chlorosulfonyl-7-ethoxycarbonylmethoxybenzofuran (yield: 68%, MS (m/z): 448 (M+), 413, 382 and 350). The obtained chlorosulfonyl compound was reacted with glycine ethyl ester hydrochloride as in Example 1 to give an ester compound (yield: 98%, MS (m/z): 515 (M+), 470, 442, 414 and 350), which was then hydrolyzed to give 2-carboxy-4-(N-carboxymethylsulfamoyl)-7-(carboxymethoxy)benzofuran (colorless needles, yield: 83%). The physical constants are shown in Table 4.

EXAMPLE 13

[Preparation of 2-carboxy-4-(N-carboxymethylsulfamoyl)-7-methoxybenzofuran (Compound No. 13)]

There was reacted 1.7 g (8.25 mmole) of 2-methoxycarbonyl-7-methoxybenzofuran with chlorosulfonic acid as in Example 1, yielding 2 g of 2-methoxycarbonyl-4-chlorosulfonyl-7-methoxybenzofuran (yield: 80%, MS (m/z): 304 (M+), 269, 238 and 210). The obtained chlorosulfonyl compound was reacted wit glycine ethyl ester hydrochloride as in Example 1 to give an ester compound (yield: 88%, MS (m/z): 371

(M+), 340, 298 and 269), which was then hydrolyzed to give 2-carboxy-4-(N-carboxymethylsulfamoyl)-7-methoxybenzofuran (colorless needles, yield: 86%). The physical constants are shown in Table 4.

EXAMPLE 14

[Preparation of 2-carboxy-4-(N-carboxymethylsulfamoyl)-7-ethoxybenzofuran (Compound No. 14)]

There was reacted 1 g (5.4 mmole) of 2-cyano-7-ethoxybenzofuran (with chlorosulfonic acid as in Example 1, yielding 0.65 g of 2-cyano-4-chlorosulfonyl-7-ethoxybenzofuran (yield: 43%, MS (m/z): 285 (M+), 257, 250 and 222). The obtained chlorosulfonyl compound was reacted with glycine ethyl ester hydrochloride as in Example 1 to give an ester compound (yield: 46%, MS (m/z): 385 (M+), 279, 250 and 222), which was then hydrolyzed, accompanying the hydrolysis of nitrile, to give 2-carboxy-4-(N-carboxymethylsulfamoyl)-7-ethoxybenzofuran (yellow prisms, yield: 62%). The physical constants are shown in Table 4.

EXAMPLE 15

[Preparation of 2-acetyl-4-(N-carboxymethylsulfamoyl)-7-methylbenzofuran (Compound No. 15)]

There was reacted 1.0 g (5.8 mmole) of 2-acetyl-7-methylbenzofuran with chlorosulfonic acid as in Example 1, yielding 0.36 g of 2-acetyl-4-chlorosulfonyl-7-methylbenzofuran (yield: 24%, MS (m/z): 232 (M+), 257, 237 and 173). The obtained chlorosulfonyl compound was reacted with glycine ethyl ester hydrochloride as in Example 1 to give an ester compound (yield: 73%, MS (m/z): 339 (M+), 266, 237 and 173), which was then hydrolyzed to give 2-acetyl-4-(N-carboxymethylsulfamoyl)-7-methylbenzofuran (yellow plates, yield: 71%). The physical constants are shown in Table 4.

EXAMPLE 16

[Preparation of 2-acetyl-4-(N-carboxymethylsulfamoyl)-7-sec-butylbenzofuran (Compound No. 6)]

There was reacted 1 g (4.6 mmole) of 2-acetyl-7-sec-butylbenzofuran with chlorosulfonic acid as in Example 1, yielding 0.97 g of 2-acetyl-4-chlorosulfonyl-7-sec-butylbenzofuran (yield: 67%, MS (m/z): 314 (M+), 285 and 186). The obtained chlorosulfonyl compound was reacted with glycine ethyl ester hyrochloride as in Example 1 to give an ester compound (yield: 82%, MS (m/z): 381 (M+), 352, 308 and 279), which was then hydrolyzed to give 2-acetyl-4-(N-carboxymethylsulfamoyl)-7-sec-butylbenzofuran (light yellow plates, yield: 73%). The physical constants are shown in Table 4.

EXAMPLE 17

[Preparation of 2-acetyl-4-(N-carboxymethylsulfamoyl)-5,6-methylenedioxybenzofuran (Compound No. 17)]

There was reacted 0.33 g (1.6 mmole) of 2-acetyl-5,6-methylenedioxybenzofuran with chlorosulfonic acid as in Example 1, yielding 0.2 g of 2-acetyl-4-chlorosulfonyl-7-methylenedioxybenzofuran (yield: 41%, MS (m/z): 302 (M+), 287, 189 and 133). The obtained chlorosulfonyl compound was reacted with glycine ethyl ester hydrochloride to give an ester compound (yield: 58%, MS (m/z): 369 (M+), 354, 296, 266 and 203), which was then hydrolyzed to give 2-acetyl-4-(N-carboxymethylsulfamoyl)-5,6-methylenedioxybenzofuran (light yellow needles, yield: 98%). The physical constants are shown in Table 4.

EXAMPLE 18

[Preparation of 2-acetyl-4-methoxy-7-(N-carboxymethylsulfamoyl)benzofuran (Compound No. 18)]

There was reacted 0.95 g (5 mmole) of 2-acetyl-4-methoxybenzofuran with chlorosulfonic acid as in Example 1, yielding 1.3 g of 2-acetyl-4-methoxy-7-chlorosulfonylbenzofuran (yield: 93%, MS (m/z): 288 (M+), 273, 253 and 189). The obtained chlorosulfonyl compound was reacted with glycine ethyl ester hydrochloride to give an ester compound (yield: 97%, MS (m/z): 354 (M+), 281, 252 and 188), which was then hydrolyzed to give 2-acetyl-4-methoxy-7-(N-carboxymethylsulfamoyl)benzofuran (yellow plates, yield: 84%). The physical constants are shown in Table 4.

EXAMPLE 19

[Preparation of 2-(4-methyl-2,5-dioxoimidazolidine-4-yl)-4-(N-carboxymethylsulfamoyl)-7-methoxybenzofuran (Compound No. 19)]

The procedure of Example 1 was repeated except that glycine-t-butyl ester hydrochloride was reacted in place of glycine ethyl ester hydrochloride to give a t-butylester compound (yield: 97%, MS (m/z): 383 (M+), 310, 282, 253 and 190). After a mixture of 0.5 g (1.3 mmole) of the obtained t-butyl ester compound, 1 g of ammonium carbonate, 1.3 g of sodium cyanide and 13 ml of 60% ethanol was stirred with heating at 55° to 60° C. for 5 hours, the resultant was made slightly acidic, which was then extracted with ethyl acetate to give 0.5 g of 2-(4-methyl-2,5-dioxoimidazolidine-4-yl)-4-(N-t-butyloxycarbonylmethylsulfamoyl)-7-methoxybenzofuran (yield: 85%) as yellow plate crystals. The obtained product was stirred in trifluoroacetic acid at room temperature to give 2-(4-methyl-2,5-dioxoimidazolidine-4-yl)-4-(N-carboxymethylsulfamoyl)-7-methoxybenzofuran (yellow plates, yield: 43%). The physical constants are shown in Table 4.

EXAMPLE 20

[Preparation of 2-(4-methyl-2,5-dioxoimidazolidine-4-yl)-4,6-di(N-carboxymethylsulfamoyl)-7-methoxylbenzofuran (Compound No. 20)]

2-Acetyl-7-methoxybenzofuran was reacted with ammonium carbonate and sodium cyanide in 60% ethanol to give 2-(4-methyl-2,5-dioxoimidazolidine-4-yl)-7-methoxybenzofuran (yield: 45%, MS (m/z): 260 (M+), 245, 189 and 174), which was then reacted with chlorosulfonic acid as in Example 1, yielding 2-(4-methyl-2,5-dioxoimidazolidine-2-yl)-4,6-dichlorosulfonyl-7-methoxybenzofuran (yield: 83%, MS (m/z): 456 (M+), 421, 385 and 350). The obtained product was reacted with glycine-t-butyl ester hydrochloride as in Example 19 to give a di-t-butyl ester compound (yield: 90%), which was treated with trifluoroacetic acid as in Example 19 to give 2-(4-methyl-2,5-dioxoimidazolidine-4-yl)-4,6-di(N-carboxymethylsulfamoyl)-7-methoxybenzofuran (colorless amorphous powder, yield: 97%). The physical constants are shown in Table 4.

EXAMPLE 21

[Preparation of 2-ethyl-3-(N-carboxymethylsulfamoyl)-5-nitrobenzofuran (Compound No. 21)]

2-Ethyl-5-nitrobenzofuran was reacted with chlorosulfonic acid as in Example 1, yielding a 3-chlorosulfonyl compound (yield: 75%, MS (m/z): 289 (M+), 254 and 191). The obtained product was reacted with glycine ethyl ester hydrochloride to give an ester compound (yield: 94%, MS (m/z): 356 (M+), 326, 310, 283 and 254), which was then hydrolyzed to give 2-ethyl-3-(N-carboxymethylsulfamoyl)-5-nitrobenzofuran (light yellow prisms, yield: 72%). The physical constants are shown in Table 4.

EXAMPLE 22

[Preparation of 2-ethyl-3-(N-carboxymethylsulfamoyl)-5-acetylaminobenzofuran (Compound No. 22)]

2-Ethyl-5-acetylaminobenzofuran was reacted with chlorosulfonic acid as in Example 1, yielding a 3-chlorosulfonyl compound (yield: 94%, MS (m/z): 301 (M+), 266, 259 and 244). The obtained product was reacted with glycine ethyl ester hydrochloride to give an ester compound (yield: 96%, MS (m/z): 368 (M+), 326, 295, 216 and 201), which was then hydrolyzed to give 2-ethyl-3-(N-carboxymethylsulfamoyl)-5-acetylaminobenzofuran (colorless prisms, yield: 50%). The physical constants are shown in Table 4.

EXAMPLE 23

[Preparation of 2-acetyl-4-(N-carboxymethylsulfamoyl)-7-p-nitrobenzyloxybenzofuran (Compound No. 23)]

2-Acetyl-7-p-nitrobenzyloxybenzofuran (3 g) was added to chlorosulfonic acid at −15° C. for 30 minutes. After the reaction mixture was stirred at −10° to −5° C. for 1 hour, the resultant was gradually added dropwise to ice-water. The solution was extracted with ethyl acetate, washed with water and dried, ethyl acetate being distilled away under reduced pressure to give 2.7 g of crude 2-acetyl-4-chlorosulfonyl-7-p-nitrobenzyloxybenzofuran.

A mixture of the chlorosulfonyl compound (1 g), glycine ethyl ester hydrochloride (0.62 g) and triethylamine (0.61 g) in dichloromethane (70 ml) was stirred at 25° to 35° C. for 5 hours, the resultant was filtered and the filtrate was distilled away. The residue was extracted with ethyl acetate and the ethyl acetate layer was washed with water and dried, ethyl acetate being distilled away under reduced pressure to give 1.5 g of a white powder, which was then purified by a silica-gel column chromatography using hexane ethyl acetate to give 1.1 g of 2-acetyl-4-(N-ethoxy-carbomethylsulfamoyl)-7-p-nitrobenzyloxybenzofuran.

The ester compound (0.3 g) was added to 1N NaOH aqueous solution (10 ml) and the mixture was stirred at normal temperature to 50° C. for 1 to 3 hours, to which 1N-HCl was added to adjust to pH 2, thereby yielding 0.25 g of a yellow powder, which was then recrystalized with methanol to give 0.2 g of 2-acetyl-4-(N-carboxymethylsulfamoyl)-7-p-nitrobenzyloxybenzofuran as light yellow prisms.

EXAMPLE 24

[Preparation of 2-acetyl-4-(N-carboxymethylsulfamoyl)-7-p-methoxybenzyloxybenzofuran (Compound No. 24)]

2-Acetyl-7-p-methoxybenzyloxybenzofuran was reacted with chlorosulfonic acid as in Example 23, yielding a 4-chlorosulfonyl compound. The obtained chlorosulfonyl compound was reacted with glycine ethyl ester hydrochloride to give an ester compound, which was then hydrolyzed to give 2-acetyl-4-(N-carboxymethylsulfamoyl)-7-p-methoxybenzyloxybnzofuran. The physical constants are shown in Table 4.

EXAMPLE 25

[Preparation of 2-acetyl-4-(N-carboxymethylsulfamoyl)-7-(2-chloropropyloxy)benzofuran (Compound No. 25)]

2-Acetyl-7-(2-chloropropyloxy)benzofuran was reacted as in Example 23 to give a chlorosulfonyl compound, which was converted to an ester compound, followed by hydrolysis to give 2-acetyl-4-(N-carboxymethysulfamoyl)-7-(2-chloropropyloxy)benzofuran. The physical constants are shown in Table 4.

EXAMPLE 26

[Preparation of 2-acetyl-4-(N-carboxymethylsulfamoyl)-7-acetonyloxybenzofuran (Compound No. 25)]

2-Acetyl-7-acetonyloxybenzofuran was reacted as in Example 23 to give a chlorosulfonyl compound, which was converted to an ester compound, followed by hydrolysis to give 2-acetyl-4-(N-carboxymethylsulfamoyl)-7-acetonyloxybenzofuran. The physical constants are shown in Table 4.

EXAMPLE 27

[Preparation of 2-acetyl-4-(N-carboxymethylsulfamoyl)-7-cyanomethyloxybenzofuran (Compound No. 27)]

2-Acetyl-7-cyanomethyloxybenzofuran was reacted as in Example 23 to give a chlorosulfonyl compound, which was converted to an ester compound, followed by hydrolysis to give 2-acetyl-4-(N-carboxymethylsulfamoyl)-7-cyanomethyloxybenzofuran. The physical constrants are shown in Table 4.

EXAMPLE 28

[Preparation of 2-acetyl-4-(N-carboxymethylsulfamoyl)-7-hydroxybenzofuran (Compound No. 28)]

A mixture of 2-acetyl-4-(N-carboxymethylsulfamoyl)-7-methoxybenzofuran and $AlCl_3$ in chlorobenzene was heated at 130° C. to give 2-acetyl-4-(N-carboxymethylsulfamoyl)-7-hydroxybenzofuran.

The physical constants are shown in Table 4.

EXAMPLE 29

[Preparation of 2-acetyl-4-(N-carboxymethylsulfamoyl)-7-benzyloxybenzofuran (Compound No. 29)]

A mixture of the 7-hydroxy compound (1.8 g) obtained in Example 28 (Compound No. 28), $K_2CO_3$ (1.6 g) and benzylbromide (2.9 g) in DMF was stirred at 80° C. for 3 hours. The reaction mixture was poured into water and extracted with ethyl acetate, which was purified by a silica-gel column chromatography to give 1.3 g of 2-acetyl-4-(N-carboxymethylsulfamoyl)-7-benzyloxybenzofuran as yellow crystals. After the obtained product was added to 20 ml of 2N-NaOH aqueous solution and the mixture was stirred for 30 minutes, the resultant was acidified to form precipitate, which was recrystallized with ethanol to give 0.4 g of 2-acetyl-4-(N-carboxymethylsulfamoyl)-7-benzyloxybenzofuran. The physical constants are shown in Table 4.

EXAMPLE 30

[Preparation of 2-acetyl-4-(N-carboxymethylsulfamoyl)-7-p-chlorobenzyloxybenzofuran (Compound No. 30)]

The procedure of Example 29 was repeated except that p-chlorobenzyl bromide was employed in place of benzyl bromide to give 2-acetyl-4-(N-carboxymethylsulfamoyl)-7-p-chlorobenzyloxybenzofuran. The physical constants are shown in Table 4.

EXAMPLE 31

[Preparation of 2-acetyl-4-(N-carboxymethylsulfamoyl)-7-allyloxybenzofuran (Compound No. 31)]

The precedure of Example 29 was repeated except that allyl bromide was employed in place of benzyl bromide to give 2-acetyl-4-(N-carboxymethyl-sulfamoyl)-7-allyloxybenzofuran. The physical constants are shown in Table 4.

EXAMPLE 32

[Preparation of 2-acetyl-4-(N-carboxymethylsulfamoyl)-7-(3-butenyloxy)benzofuran (Compound No. 32)]

The precedure of Example 29 was repeated except that 4-bromo-1-butene was employed in place of benzyl bromide to give 2-acetyl-4-(N-carboxymethylsulfamoyl)-7-(3-butenyloxy)benzofuran. The physical constants are shown in Table 4.

EXAMPLE 33

[Preparation of 2-acetyl-4-(N-p-methoxybenzyl-N-carboxymethylsulfamoyl)-7-p-methoxybezyloxybenzofuran (Compound No. 33)]

A mixture of 7-hydroxy compound (1.2 g) obtained in Example 28 (Compound No. 28), K$_2$CO$_3$ (1.8 g) and p-methoxybenzyl chloride (2.3 g) in DMF (70 ml) was stirred at 25° to 50° C. for 3 hours. The oil obtained by treating the reaction mixture was purified by a silica-gel column chromatography (eluent: cyclohexane ethyl acetate) to give 1.1 g of 2-acetyl-4-(N-p-methoxybenzyl-N-carbo-p-methoxybenzyloxymethylsulfamoyl)-7-p-methoxybenzyloxybenzofuran. After hydrolyzing the obtained product in 20 ml of 2N NaOH aqueous solution, the resultant was acidified to form precipitate, which was recrystallized with DMSO-water to give 0.5 g of 2-acetyl-4-(N-p-methoxybenzyl-N-carboxymethylsulfamoyl)-7-p-methoxybenzyloxybenzofuran. The physical constants are shown in Table 4.

EXAMPLE 34

[Preparation of 2-acetyl-4-(N-p-chlorobenzyl-N-carboxymethylsulfamoyl)-7-p-chlorobenzyloxybenzofuran (Compound No. 34)]

The procedure of Example 33 was repeated except that p-chlorobenzylchloride was employed in place of p-methoxybenzyl chloride to give 2-acetyl-4-(N-p-chlorobenzyl-N-carboxymethylsulfamoyl)-7-p-chlorobenzyloxybenzofuran. The physical constants are shown in Table 4.

EXAMPLE 35

[Preparation of 2-acetyl-4-(N-benzyl-N-carboxymethylsulfamoyl)-7-benzyloxybenzofuran (Compound No. 35)]

The procedure of Example 33 was repeated except that benzyl bromide was employed in place of p-methoxybenzyl chloride to give 2-acetyl-4-(N-benzyl-N-carboxymethylsulfamoyl)-7-benzyloxybenzofuran. The physical constants are shown in Table 4.

EXAMPLE 36

[Preparation of sodium salt of 2-ethyl-3-(N-carboxymethylsulfamoyl)-5-acetylaminobenzofuran (Compound No. 22)]

There was dissolved 30 mg (0.088 mmole) of the compound obtained in Example 22 (Compound No. 22) into 0.9 ml of 0.1N NaOH aqueous solution, which was lyophilized to give quantitatively Na salt as a yellow powder (mp: 275° to 279° C. (dec)).

The procedure was repeated to give sodium salts of the Compound Nos. 1 to 21.

EXAMPLE 37

[Preparation of potassium salt of 2-ethyl-3-(N-carboxymethylsulfamoyl)-5-acetylaminobenzofuran (Compound No. 22)]

There was dissolved 30 mg (0.088 mmole) of the compound obtained in Example 22 (Compound No. 22) into 0.88 ml of 0.1N KOH aqueous solution, which was lyophilized to give quantitatively K salt as a yellow powder (mp: 283° to 287° C. (dec.)).

The procedure was repeated to give potassium salts of the Compound Nos. 1 to 21.

EXAMPLE 38

[Preparation of sodium salt of 2-acetyl-4-(N-carboxymethylsulfamoyl)-7-p-nitrobenzyloxybenzofuran (Compound No. 23)]

There was dissolved 45 mg of the compound obtained in Example 23 (Compound No. 23) into 1 ml of 0.1N NaOH aqueous solution, which was lyophilized to give quantiatatively Na salt as a yellow powder (mp: not less than 280° C.).

The procedure was repeated to give sodium salts of the Compound Nos. 24 to 35.

EXAMPLE 39

[Preparation of potassium salt of 2-acetyl-4-(N-carboxymethylsulfamoyl)-7-p-nitrobenzyloxybenzofuran (Compound No. 23)]

There was dissolved 45 mg of the compound obtained in Example 23 (Compound No. 23) into 1 ml of 0.1N KOH aqueous solution, which was lyophilized to give quantitatively K salt as a yellow powder (mp: not less than 280° C.).

The procedure was repeated to give sodium salts of the Compound Nos. 24 to 35.

EXAMPLE 40

A tablet of 100 mg having the following composition was prepared.

| (Component) | (mg) |
|---|---|
| 2-Acetyl-4-(N—carboxymethylsulfamoyl)-7-n-butyloxybenzofuran | 100 |
| Lactose | 25 |
| Corn starch | 45 |
| Crystal cellulose | 15 |
| Methyl cellulose | 3 |
| Calcium stearate | 2 |

EXAMPLE 41

A tablet of 100 mg having the following composition was prepared.

| (Component) | (mg) |
|---|---|
| 2-Acetyl-4-(N—carboxymethylsulfamoyl)-7-p-nitrobenzyloxybenzofuran | 100 |
| Lactose | 25 |
| Corn starch | 45 |
| Crystal cellulose | 15 |
| Methyl cellulose | 3 |
| Calcium stearate | 2 |

EXAMPLE 42

A capsule of 100 mg having the following composition was prepared by filling the mixture of the components in capsule 5.

| (Component) | (mg) |
|---|---|
| 2-Acetyl-4-(N—carboxymethylsulfamoyl)-7-n-pentyloxybenzofuran | 10 |
| Lactose | 45 |
| Corn starch | 35 |
| Crystal cellulose | 8 |
| Calcium stearate | 2 |

EXAMPLE 43

A cupsule of 100 mg having the following composition was prepared by filling the mixture of the components in capsule 5.

| (Component) | (mg) |
|---|---|
| 2-Acetyl-4-(N—carboxymethylsulfamoyl)-7-p-nitrobenzyloxybenzofuran | 10 |
| Lactose | 45 |
| Corn starch | 35 |
| Crystal cellulose | 8 |
| Calcium stearate | 2 |

EXAMPLE 44

The following components were mixed together. After making the core by a slug machine, it was granulated and screened. Thereafter, masking was made with Tc-5R (film coatings) and 500 mg of granules having 20 to 40 meshs were prepared.

| (Component) | (mg) |
|---|---|
| 2-Acetyl-4-(N—carboxymethylsulfamoyl)-7-n-hexyloxybenzofuran | 10 |
| Lactose | 355 |
| Calcium hydrogenphosphate | 80 |
| Crystal cellulose | 40 |
| Calcium stearate | 5 |
| Tc-5R | 10 |

EXAMPLE 45

According to the following formulation the procedures in Example 44 were repeated to prepare 500 mg of a granules.

| (Component) | (mg) |
|---|---|
| 2-Acetyl-4-(N—carboxymethylsulfamoyl)-7-p-nitrobenzyloxybenzofuran | 10 |
| Lactose | 355 |
| Calcium hydrogenphosphate | 80 |
| Crystal cellulose | 40 |
| Calcium stearate | 5 |
| Tc-5R | 10 |

EXAMPLE 46

There was dissolved 1 mg of sodium salt of 2-acetyl-4-(N-carboxymethylsulfamoyl)-7-n-heptyloxybenzofuran in 1 ml of a physiological saline, which was adjusted at pH 7.0 to prepare injections.

EXAMPLE 47

There was dissolved 1 mg of sodium salt of 2-acetyl-4-(N-carboxymethylsulfamoyl)-7-p-nitrobenzyloxybenzofuran in 1 ml of physiological saline, which was adjusted at pH 7.0 to prepare injections.

TABLE 4

| Compound No. | Structural formula (A:SO$_2$NHCH$_2$COOH) | Mp (°C.) | $^1$H—HMR (δ, solvent: DMSO—d$_6$ = D) | EA Empirical formula C (%) Calcd. (Found) | H (%) Calcd. (Found) | MS (m/z) | (IR) |
|---|---|---|---|---|---|---|---|
| 1 | 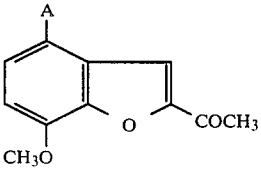 | 223 to 225 | 2.48 (3H, S, COCH$_3$), 3.45 (2H, br d, NHCH$_2$), 3.52 (1H, br s, COOH), 3.90 (3H, s, OCH$_3$), 7.03 (1H, d, 6-H), 7.58 (1H, d, 5-H), 7.70 (1H, br s, NH), 7.92 (1H, s, 3-H), D | C$_{13}$H$_{13}$NO$_7$S 47.70 (47.78) | 4.00 (3.89) | 327(M$^+$), 282, 253, 189 | |

TABLE 4-continued

| Compound No. | Structural formula (A:SO₂NHCH₂COOH) | Mp (°C.) | ¹H—HMR (δ, solvent: DMSO—d₆ = D) | EA Empirical formula C (%) Calcd. (Found) | H (%) Calcd. (Found) | MS (m/z) | (IR) |
|---|---|---|---|---|---|---|---|
| 2 | 4-A, 7-C₂H₅O-benzofuran-2-COCH₃ | 143 to 145 | 1.35 (3H, t, C$\underline{H_3}$CH₂), 2.43 (3H, s, COCH₃), 3.35 (1H, br s, COOH), 3.38 (2H, br d, NHC$\underline{H_2}$), 4.08 (2H, q, CH₃C$\underline{H_2}$), 6.93 (1H, d, 6-H), 7.42 (1H, d, 5-H), 7.78 (1H, s, 3-H), 7.90 (1H, br s, NH), D | $C_{14}H_{15}NO_7S$ 49.26 (49.38) | 4.43 (4.41) | n.d. | |
| 3 | 4-A, 7-CH₃(CH₂)₂O-benzofuran-2-COCH₃ | 202 to 205 | 0.99 (3H, t, C$\underline{H_3}$CH₂), 1.66 (2H, m, $\overline{CH_3C}$$\underline{H_2}$), 2.47 (3H, s, COCH₃), 3.43 (2H, br d, NHC$\underline{H_2}$), 3.58 (1H, br s, COOH), 4.04 (2H, t, CH₂O), 6.98 (1H, d, 6-H), 7.46 (1H, d, 5-H), 7.83 (1H, s, 3-H), 7.94 (1H, br s, NH), D | $C_{15}H_{17}NO_7S$ 50.70 (51.09) | 4.82 (4.76) | 355(M⁺), 313, 267, 239 | |
| 4 | 4-A, 7-CH₃(CH₂)₃O-benzofuran-2-COCH₃ | 163 to 164 | 0.95 (3H, t, CH₂C$\underline{H_3}$), 1.40 to 1.73 (4H, m, C$\underline{H_2}$C$\underline{H_2}$CH₃), 2.47 (3H, s, COCH₃), 3.44 (2H, br d, NHC$\underline{H_2}$), 3.55 (1H, br s, COOH), 4.07 (2H, t, OCH₂), 6.90 (1H, d, 6-H), 7.36 (1H, d, 5-H), 7.72 (1H, s, 3-H), 7.80 (1H, br s, NH), D | $C_{16}H_{19}NO_7S$ 52.03 (52.19) | 5.18 (5.11) | 369(M⁺), 313, 239 | 3270, 1737, 1682, 1167 |
| 5 | 4-A, 7-CH₃(CH₂)₄O-benzofuran-2-COCH₃ | 171 to 173 (dec) | 0.83 (3H, t, C$\underline{H_3}$CH₂), 1.20 to 1.40 (4H, m, CH₃C$\underline{H_2}$CH₂), 1.60 to 1.80 (2H, m, C$\underline{H_2}$CH₂O), 2.45 (3H, s, COCH₃), 3.41 (2H, br d, NHC$\underline{H_2}$), 3.52 (1H, br s, COOH), 4.06 (2H, t, OCH₂), 6.97 (1H, d, 6-H), 7.45 (1H, d, 5-H), 7.83 (1H, s, 3-H), 7.90 (1H, br s, NH), D | $C_{17}H_{21}NO_7S$ 53.25 (53.41) | 5.52 (5.39) | 383(M⁺), 313, 268, 239 | |
| 6 | 4-A, 7-CH₃(CH₂)₅O-benzofuran-2-COCH₃ | 204 to 207 | 0.89 (3H, t, CH₂C$\underline{H_3}$), 1.05 to 1.80 (8H, m, CH₃CH₂CH₂CH₂CH₂), 2.40 (3H, s, COCH₃), 3.30 (1H, br s, COOH), 3.35 (2H, br d, NHC$\underline{H_2}$), 4.24 (2H, t, OCH₂), 6.68 (1H, d, 6-H), 7.31 (1H, d, 5-H), 7.72 (1H, s, 3-H), 7.82 (1H, br s, NH), D | $C_{18}H_{23}NO_7S$ 54.40 (54.11) | 5.83 (5.72) | 397(M⁺), 313, 268, 239 | |
| 7 | 4-A, 7-CH₃(CH₂)₆O-benzofuran-2-COCH₃ | 165 to 166 | 0.80 (3H, t, CH₂C$\underline{H_3}$), 1.24 (8H, m, (C$\underline{H_2}$)₄CH₃), 1.72 (2H, m, OCH₂C$\underline{H_2}$), 2.44 (3H, s, COCH₃), 3.40 (2H, br d, NHC$\underline{H_2}$), 4.06 (2H, t, OCH₂), 5.39 (1H, br s, COOH), 7.00 (1H, d, 6-H), 7.46 (1H, d, 5-H), 7.80 (1H, br s, NH), 7.82 (1H, s, 3-H), D | $C_{19}H_{25}NO_7S$ 55.46 (55.39) | 6.12 (6.10) | 411(M⁺), 313, 239 | |

TABLE 4-continued

| Compound No. | Structural formula (A:SO$_2$NHCH$_2$COOH) | Mp (°C.) | $^1$H—HMR (δ, solvent: DMSO—d$_6$ = D) | EA Empirical formula C (%) Calcd. (Found) | H (%) Calcd. (Found) | MS (m/z) | (IR) |
|---|---|---|---|---|---|---|---|
| 8 | A, benzofuran with OCH$_2$COOH at 7-position and COCH$_3$ at 2-position | 332 to 235 | 2.51 (3H, s, COCH$_3$), 3.20 (2H, br s, COOH×2), 3.47 (2H, s, NHCH$_2$), 4.92 (2H, s, OCH$_2$), 7.07 (1H, s, 6-H), 7.59 (1H, d, 5-H), 7.98 (1H, s, 3-H), 8.14 (1H, br s. NH), D | C$_{14}$H$_{13}$NO$_9$S 45.29 (45.10) | 3.53 (3.59) | 371(M$^+$), 326, 312, 297 | |
| 9 | SO$_2$N(CH$_3$)—CH$_2$COOH, benzofuran with CH$_3$(CH$_2$)$_3$O and COCH$_3$ | 101 to 103 | 0.87 (3H, t, CH$_3$CH$_2$), 1.10 to 1.80 (4H, m, CH$_3$CH$_2$CH$_2$), 2.45 (3H, s, COCH$_3$), 2.64 (3H, s, N—CH$_3$), 3.55 (1H, br s, COOH), 3.74 (2H, s, NCH$_2$), 4.09 (2H, t, CH$_2$O), 7.01 (1H, d, 6-H), 7.46 (1H, d, 5-H), 7.66 (1H, s, 3-H), D | C$_{17}$H$_{21}$NO$_7$S 53.25 (53.10) | 5.52 (5.57) | 383(M$^+$), 338, 295 281, 239 | 1285 Nujol |
| 10 | SO$_2$N(CH$_3$)—CH(CH$_3$)COOH, benzofuran with O(CH$_2$)$_3$CH$_3$ and COCH$_3$ | 147 to 150 | 0.90 (3H, t, CH$_3$CH$_2$), 1.09 (3H, d, CH$_3$CH), 1.25 to 1.88 (4H, m, CH$_3$CH$_2$CH$_2$) 2.44 (3H, s, COCH$_3$) 2.58 (3H, s, NCH$_3$), 3.75 (1H, br, s, COOH), 4.05 (2H, t, OCH$_2$), 4.48 (1H, q, CH$_3$), 7.00 (1H, d, 6-H), 7.48 (1H, d, 5-H), 7.68 (1H, s, 3-H), D | C$_{18}$H$_{23}$NO$_7$S 54.40 (54.63) | 5.83 (5.72) | 397(M$^+$) 353, 296 239 | 1287 Nujol |
| 11 | SO$_2$NHCH(CH$_3$)COOH, benzofuran with O(CH$_2$)$_3$CH$_3$ and COCH$_3$ | 181 to 183 | 0.86 (3H, t, CH$_3$CH$_2$), 1.04 (3H, d, CH$_3$CH) 2.40 (3H, s, COCH$_3$) 3.30 (1H, br, s, COOH), 3.50 (1H, m, CHCH$_3$), 3.98 (2H, t, OCH$_2$), 6.86 (1H, d, 6-H), 7.32 (1H, d, 5-H), 7.70 (1H, s, 3-H), 7.88 (1H, br, d, NH), D | C$_{17}$H$_{21}$NO$_7$S 53.25 (53.49) | 5.52 (5.50) | 383(M$^+$) 338, 295 239 | 1284 Nujol |
| 12 | A, benzofuran with OCH$_2$COOH and COOH | 265 to 269 (dec) | 3.32 (2H, br d, NHCH$_2$), 3.70 (3H, br s, COOH×3), 4.70 (2H, s, OCH$_2$), 6.80 (1H, d, 6-H), 7.33 (1H, d, 5-H), 7.53 (1H, s, 3-H), 7.88 (1H, br s, NH), D | C$_{13}$H$_{11}$NO$_{10}$S 41.83 (41.70) | 2.87 (2.99) | n.d. | |
| 13 | A, benzofuran with CH$_3$O and COOH | 264 to 267 (dec) | 3.20 (2H, br s, COOH×2), 3.37 (2H, br d, NHCH$_2$), 3.39 (3H, s, CH$_3$O), 6.96 (1H, d, 6-H), 7.58 (1H, d, 5-H), 7.60 (1H, s, 3-H), 7.82 (1H, br s, NH), D | C$_{12}$H$_{11}$NO$_8$S 43.77 (43.51) | 3.37 (3.39) | 329(M$^+$) 284, 255, 191 | |
| 14 | A, benzofuran with C$_2$H$_5$O and COOH | 221 to 224 | 1.34 (t, CH$_3$), 3.35 (2H, br d, NHCH$_2$), 3.73 (2H, br s, COOH×2), 4.07 (2H, q, CH$_3$CH$_2$), 6.88 (1H, d, 6-H), 7.39 (1H, d, 5-H), 7.59 (1H, s, 3-H), 7.92 (1H, br t, NH), D | C$_{13}$H$_{13}$NO$_8$S 45.48 (45.70) | 3.82 (3.80) | 343(M$^+$) 298, 269, 241 | |

TABLE 4-continued

| Compound No. | Structural formula (A:SO$_2$NHCH$_2$COOH) | Mp (°C.) | $^1$H—HMR (δ, solvent: DMSO—d$_6$ = D) | EA Empirical formula C (%) Calcd. (Found) | H (%) Calcd. (Found) | MS (m/z) | (IR) |
|---|---|---|---|---|---|---|---|
| 15 | 4-A, 7-CH$_3$ benzofuran-2-COCH$_3$ | 193 to 196 (dec) | 2.38 (3H, s, 7-CH$_3$), 2.43 (2H, s, COCH$_3$), 3.38 (2H, br d, NHCH$_2$), 3.65 (1H, br s, COOH), 7.15 (1H, d, 6-H), 7.35 (1H, d, 5-H), 7.74 (1H, s, 3-H), 7.95 (1H, br s, NH), D | C$_{13}$H$_{13}$NO$_6$S 50.17 (50.02) | 4.21 (4.29) | 311(M$^+$), 266, 237, 173 | |
| 16 | 4-A, 7-CH(CH$_3$)CH$_2$CH$_3$ benzofuran-2-COCH$_3$ | 171 to 174 | 0.76 (3H, t, CH$_2$CH$_3$), 1.27 (3H, d, CHCH$_3$), 1.66 (2H, m, CH$_2$), 2.47 (3H, s, COCH$_3$), 3.08 (1H, m, CH), 3.46 (2H, br s, NHCH$_2$), 3.70 (1H, br s, COOH), 7.36 (1H, d, 6-H), 7.52 (1H, d, 5-H), 7.85 (1H, s, 3-H), 8.08 (1H, br s, NH), D | C$_{16}$H$_{19}$NO$_6$S 54.38 (54.22) | 5.42 (5.31) | 353(M$^+$), 324, 279 | |
| 17 | methylenedioxy benzofuran-2-COCH$_3$ | 240 to 244 (dec) | 2.33 (3H, s, COCH$_3$), 3.55 (2H, br s, NHCH$_2$), 3.62 (1H, br s, COOH), 5.92 (2H, s, OCH$_2$O), 7.08 (1H, s, 7-H), 7.53 (1H, s, 3-H), 7.70 (1H, br s, NH), acetone-d$_6$ | C$_{13}$H$_{11}$NO$_8$S 45.75 (46.01) | 3.25 (3.30) | 341(M$^+$), 326, 266, 203, 189 | |
| 18 | 4-OCH$_3$, 7-A benzofuran-2-COCH$_3$ | 184 to 188 (dec) | 2.46 (3H, s, OCH$_3$), 3.66 (2H, br d, NHCH$_2$), 3.75 (1H, br s, COOH), 3.85 (3H, s, COCH$_3$), 5.79 (1H, d, 5-H), 7.65 (1H, d, 6-H), 7.74 (1H, s, 3-H), 7.90 (1H, br s, NH), D | C$_{13}$H$_{13}$NO$_7$S 47.70 (47.61) | 4.00 (4.09) | 327(M$^+$), 282, 253, 189 | |
| 19 | 4-A, 7-CH$_3$O benzofuran-2-hydantoin | 254 to 258 (dec) | 1.69 (3H, s, CCH$_3$), 3.38 (2H, br d, COOH), 3.83 (3H, s, CH$_3$O), 6.92 (1H, d, 6-H), 7.00 (1H, br s, COOH), 7.10 (1H, s, 3-H), 7.47 (1H, d, 4-H), 7.96 (1H, br s, NHCH$_2$), 8.51 (1H, br s, ring NH), 10.88 (1H, br s, ring NH), D | C$_{15}$H$_{15}$N$_3$O$_8$S 45.34 (45.60) | 3.81 (3.72) | n.d. | |
| 20 | 4,6-A, 7-OCH$_3$ benzofuran-2-hydantoin | 198 to 200 (dec) | 1.70 (3H, s, CH$_3$), 3.38 (2H, br d, CH$_2$), 3.52 (2H, br d, CH$_2$), 4.16 (3H, s, OCH$_3$), 5.60 (2H, br s, COOH×2), 7.12 (1H, s, 3-H), 5.24 (1H, s, 5-H), 8.10 (2H, br d, HN×2), 8.56 (1H, s, ring NH), 11.00 (1H, br s, ring NH), D | C$_{17}$H$_{18}$N$_4$O$_{12}$S$_2$ 38.20 (38.01) | 3.39 (3.47) | n.d. | |
| 21 | 5-NO$_2$, 3-A benzofuran-2-C$_2$H$_5$ | 137 to 139 | 1.25 (3H, t, CH$_3$), 3.05 (2H, q, CH$_2$CH$_3$), 3.35 (1H, br s, COOH), 3.63 (2H, br d, NHCH$_2$), 7.78 (1H, d, 7-H), 8.18 (1H, d, 6-H), 8.45 (1H, br s, NH), 8.60 (1H, s, 4-H), D | C$_{12}$H$_{12}$N$_2$O$_7$S 43.90 (43.59) | 3.68 (3.70) | 328(M$^+$), 283, 254, 189, 143 | |

TABLE 4-continued

| Compound No. | Structural formula (A:SO₂NHCH₂COOH) | Mp (°C.) | ¹H—HMR (δ, solvent: DMSO—d₆ = D) | EA Empirical formula C (%) Calcd. (Found) | H (%) Calcd. (Found) | MS (m/z) | (IR) |
|---|---|---|---|---|---|---|---|
| 22 | CH₃CONH- (benzofuran with A at 3-position, C₂H₅ at 2-position) | 254 to 256 (dec) | 1.21 (3H, t, CH₂C$\underline{H}$₃), 1.94 (3H, s, COC$\underline{H}$₃), 2.90 (2H, q, C$\underline{H}$₂CH₃), 3.40 (1H, br s, COOH), 3.48 (2H, d, NHC$\underline{H}$₂), 7.26 (1H, d, 7-H), 7.40 (1H, d, 6-H), 7.74 (1H, s, 4-H), 8.00 (1H, t, N$\underline{H}$CH₂), 9.82 (1H, s, CON$\underline{H}$), D | $C_{14}H_{16}N_2O_6S$ 49.41 (49.58) | 4.74 (4.69) | 340(M⁺), 298, 267, 204, 160 | |
| 23 | A-benzofuran-COCH₃ with OCH₂—C₆H₄—NO₂ | 157 to 159 | 2.45 (3H, s, CH₃), 3.40 (2H, d, NHC$\underline{H}$₂), 5.33 (2H, s, OCH₂), 7.01 (1H, d, 6-H), 7.42 (1H, d, 5-H), 7.48 (2H, d, 2' and 6'-H), 7.78 (1H, s, 3-H), 7.92 (1H, t, NH), 7.96 (2H, d, 3' and 5'-H), D | $C_{19}H_{16}N_2O_9S$ 50.89 (51.01) | 3.60 (3.32) | 448(M⁺), 402, 389, 373, 310 | |
| 24 | A-benzofuran-COCH₃ with OCH₂—C₆H₄—OCH₃ | 178 to 180 | 2.41 (3H, s, CH₃), 3.40 (2H, d, NHC$\underline{H}$₂), 5.27 (2H, s, OCH₂), 6.98 (1H, d, 6-H), 7.42 (1H, d, 5-H), 7.29 (2H, d, 2' and 6'-H), 7.67 (2H, d, 3' and 5'-H), 7.77 (1H, s, 3-H), 7.93 (1H, t, NH), D | $C_{20}H_{19}O_8NS$ 55.42 (55.33) | 4.42 (4,28) | n.d. | |
| 25 | A-benzofuran-COCH₃ with OCH₂CHClCH₃ | 203 to 205 | 1.38 (3H, d, CH—CH₃), 2.38 (3H, s, COCH₃), 3.41 (2H, d, NHCH₃), 3.55 (2H, d, OC$\underline{H}$₂), 4.95 (1H, m, OCH₂C$\underline{H}$), 6.93 (1H, d, 6-H), 7.41 (1H, d, 5-H), 7.89 (1H, s, 3-H), 7.86 (1H, t, NH), D | $C_{15}H_{16}ClNO_7S$ 46.22 (46.28) | 4.14 (4.26) | 389(M⁺), 354, 326 | |
| 26 | A-benzofuran-COCH₃ with OCH₂COCH₃ | 97 to 99 | 2.06 (3H, s, OCH₂COC$\underline{H}$₃), 2.43 (3H, s, COCH₃), 3.37 (2H, d, NHC$\underline{H}$₂), 3.51 (1H, br s, COOH), 4.92 (2H, s, OC$\underline{H}$₂COCH₃), 6.70 (1H, d, 6-H), 7.33 (1H, d, 5-H), 7.73 (1H, s, 3-H), 7.88 (1H, t, NH), D | $C_{15}H_{15}O_8NS$ 48.78 (48.61) | 4.09 (4.25) | 369(M⁺), 326, 310 | |
| 27 | A-benzofuran-COCH₃ with OCH₂CN | 233 to 235 | 2.50 (3H, s, COCH₃), 3.31 (2H, d, NHC$\underline{H}$₂), 3.55 (1H, br s, COOH), 5.01 (2H, s, OCH₂), 6.61 (1H, d, 6-H), 7.51 (1H, d, 5-H), 7.80 (1H, s, 3-H), 7.98 (1H, t, NH), D | $C_{14}H_{12}O_7N_2S$ 47.73 (48.20) | 3.43 (3.37) | n.d. | |
| 28 | A-benzofuran-COCH₃ with HO- | not less than 280 | 2.40 (3H, s, —COCH₃), 3.38 (2H, d, NHC$\underline{H}$₂), 3.50 (1H, br s, COOH), 6.80 (1H, d, 6-H), 7.40 (1H, d, 5-H), 7.60 (1H, br s, NH), 7.80 (1H, s, 3-H), D | $C_{14}H_{11}NO_7S$ 46.01 (46.26) | 3.54 (3.66) | n.d. | |

TABLE 4-continued

| Compound No. | Structural formula (A:SO₂NHCH₂COOH) | Mp (°C.) | ¹H—HMR (δ, solvent: DMSO—d₆ = D) | EA Empirical formula C (%) Calcd. (Found) | H (%) Calcd. (Found) | MS (m/z) | (IR) |
|---|---|---|---|---|---|---|---|
| 29 | benzofuran with A at 4-position, COCH₃ at 2-position, OCH₂-phenyl at 7-position | 135 to 137 (dec) | 2.50 (3H, s, COC$\underline{H}_3$), 3.40 (2H, d, NHC$\underline{H}_2$), 3.55 (1H, br s, COOH), 5.10 (2H, s, —OC$\underline{H}_2$-phenyl), 6.7 to 7.35 (7H, m, 5,6-H and -phenyl), 7.63 (1H, s, 3-H), 7.80 (1H, t, NH), D | $C_{19}H_{17}NO_7S$ 56.57 (56.37) | 4.25 (4.14) | 403(M⁺), 358, 326 | |
| 30 | benzofuran with A at 4-position, COCH₃ at 2-position, OCH₂-C₆H₄-Cl at 7-position | 178 to 180 (dec) | 2.60 (3H, s, —COC$\underline{H}_3$), 3.42 (2H, d, NHC$\underline{H}_2$COO), 3.50 (1H, br s, COOH), 5.12 (2H, s, OC$\underline{H}_2$-C₆H₄-Cl), 6.90 (1H, d, 6-H), 7.00 to 7.25 (4H, m, -C₆H₄-Cl), 7.30 (1H, s, 5-H), 7.63 (1H, s, 3-H), 7.80 (1H, t, NH), D | $C_{19}H_{16}NO_7SCl$ 52.12 (52.30) | 3.68 (3.76) | 437(M⁺), 326 | |
| 31 | benzofuran with A at 4-position, COCH₃ at 2-position, OCH₂CH=CH₂ at 7-position | 190 to 192 (dec) | 2.55 (3H, s, COC$\underline{H}_3$), 3.45 (2H, d, NHC$\underline{H}_2$COO), 3.55 (1H, br s, COOH), 4.63 (2H, d, —OC$\underline{H}_2$CH=CH₂), 5.05 to 5.35 (2H, d,d, —OCH₂CH=C$\underline{H}_2$), 5.60 to 6.03 (1H, m, —OCH₂C$\underline{H}$=CH₂), 6.50 (1H, d, 6-H), 7.35 (1H, d, 5-H), 7.65 (1H, s, 3-H), 7.83 (1H, t, NH), D. | $C_{15}H_{15}NO_7S$ 50.99 (51.12) | 4.28 (4.31) | 352(M⁺), 278 | |
| 32 | benzofuran with A at 4-position, COCH₃ at 2-position, OCH₂CH₂CH=CH₂ at 7-position | 169 to 171 | 2.20 to 2.63 (2H, m, —OCH₂C$\underline{H}_2$CH=CH₂), 2.50 (3H, s, COC$\underline{H}_3$), 3.45 (2H, d, —NHC$\underline{H}_2$COO), 3.50 (1H, br s, COOH), 4.15 (2H, t, —OC$\underline{H}_2$CH₂CH=CH₂), 4.78 to 5.08 (2H, m, —OCH₂CH₂CH=C$\underline{H}_2$), 5.2 to 5.8 (1H, m, —OCH₂CH₂C$\underline{H}$=CH₂), 6.85 (1H, d, 6-H), 7.32 (1H, d, 5-H), 7.63 (1H, s, 3-H), 7.75 (1H, t, —NH), D | $C_{16}H_{17}NO_7S$ 52.31 (52.03) | 4.66 (4.50) | 367(M⁺), 313, 239 | |

TABLE 4-continued

| Compound No. | Structural formula (A:SO$_2$NHCH$_2$COOH) | Mp (°C.) | $^1$H—HMR (δ, solvent: DMSO—d$_6$ = D) | EA Empirical formula C (%) Calcd. (Found) | H (%) Calcd. (Found) | MS (m/z) | (IR) |
|---|---|---|---|---|---|---|---|
| 33 |  | 271 to 274 | 2.45 (3H, s, COCH$_3$), 3.39 (1H, br s, COOH), 3.54 (3H, s, OCH$_3$), 3.57 (3H, s, OCH$_3$), 3.85 (2H, s, —NCH$_2$CO), 4.62 (2H, s, NC$\underline{H}_2$C$_6$H$_4$), 5.16 (2H, s, —OCH$_2$), 6.57 to 7.03 (8H, m, benzylphenyl H), 7.18 (1H, d, 5-H), 7.65 (1H, d, 6-H), 7.76 (1H, s, 3-H), D | C$_{28}$H$_{27}$NO$_9$S 60.75 (60.39) | 4.92 (4.71) | 553(M$^+$), 494 | |
| 34 | 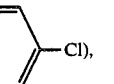 | 168 to 170 (dec) | 2.40 (3H, s, COCH$_3$), 3.45 (1H, br s, COOH), 3.78 (2H, s, NCH$_2$COO), 4.25 (2H, s, NCH$_2$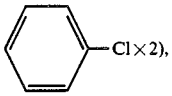—Cl), 5.18 (2H, s, —OCH$_2$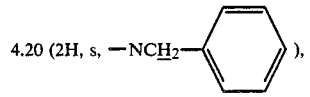—Cl), 6.85 to 7.55 (10H, m, 5,6-H, 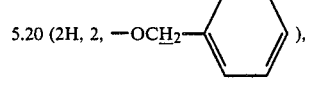—Cl×2), 7.60 (1H, s, 3-H), D | C$_{26}$H$_{21}$NCl$_2$O$_7$S 55.53 (55.39) | 3.76 (3.92) | 561(M$^+$), 516 | |
| 35 |  | 144 to 146 (dec) | 2.43 (3H, s, COCH$_3$), 3.50 (1H, br s, COOH), 3.70 (2H, s, NCH$_2$COO), 4.20 (2H, s, —NC$\underline{H}_2$—⌬ ), 5.20 (2H, 2, —OC$\underline{H}_2$—⌬ ), 6.80 to 7.50 (12H, m, 5,6-H, and —⌬ ×2), 7.60 (1H, s, 3-H), D | C$_{26}$H$_{23}$NO$_7$S 63.28 (63.22) | 4.70 (4.66) | 493(M$^+$), 434 | |

What we claim is:

1. A benzofuran derivative having the formula (I):

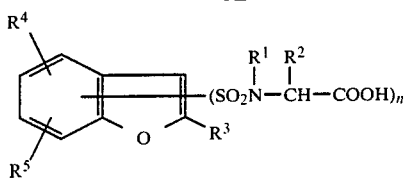

wherein $R^1$ is hydrogen atom, a benzyl group, unsubstituted or substituted with a halogen atom or an alkyloxy group, or an alkyl group having 1 to 3 carbon atoms, $R^2$ is hydrogen atom or an alkyl group having 1 to 3 carbon atoms, $R^3$ is acetyl group, ethyl group, carboxyl group or 4-methyl-2,5-dioxoimidazolidine-4-yl group, $R^4$ is hydrogen atom, hydroxyl group, an alkyl group having 1 to 6 carbon atoms, an alkoxy group having 1 to 9 carbon atoms, carboxymethoxy group, nitro group, acetoamino group, a benzyloxy group, unsubstituted or substituted with a halogen atom, nitro group or an alkyloxy group, or a group having the formula: $-OR^6$, wherein $R^6$ is an alkenyl group having 2 to 4 carbon atoms or an alkyl group having 2 to 3 carbon atoms having a halogen atom, cyano group or oxo group, $R^5$ is hydrogen atom or methylenedioxy group together with $R^4$ group, n is 1 or 2, and the unsubstituted or substituted N-carboxymethylsulfamoyl group, $R^4$ and $R^5$ are attached at 3-position, 4-position, 5-position, 6-position or 7-position of the benzofuran ring, or a nontoxic salt thereof.

2. The benzofuran derivative or a nontoxic salt thereof of claim 1, wherein the derivative is 2-acetyl-4-(N-carboxymethylsulfamoyl)-7-methoxybenzofuran.

3. The benzofuran derivative or a nontoxic salt thereof of claim 1, wherein the derivative is 2-acetyl-4-(N-carboxymethylsulfamoyl)-7-ethoxybenzofuran.

4. The benzofuran derivative or a nontoxic salt thereof of claim 1, wherein the derivative is 2-acetyl-4-(N-carboxymethylsulfamoyl)-7-n-propoxybenzofuran.

5. The benzofuran derivative or a nontoxic salt thereof of claim 1, wherein the derivative is 2-acetyl-4-(N-carboxymethylsulfamoyl)-7-n-butoxybenzofuran.

6. The benzofuran derivative of a nontoxic salt thereof of claim 1, wherein the derivative is 2-acetyl-4-(N-carboxymethylsulfamoyl)-7-n-pentyloxybenzofuran.

7. The benzofuran derivative or a nontoxic salt thereof of claim 1, wherein the derivative is 2-acetyl-4-(N-carboxymethylsulfamoyl)-7-n-hexyloxybenzofuran.

8. The benzofuran derivative or a nontoxic salt thereof of claim 1, wherein the derivative is 2-acetyl-4-(N-carboxymethylsulfamoyl)-7-n-heptyloxybenzofuran.

9. The benzofuran derivative or a nontoxic salt thereof of claim 1, wherein the derivative is 2-acetyl-4-(N-carboxymethylsulfamoyl)-7-carboxymethoxybenzofuran.

10. The benzofuran derivative or a nontoxic salt thereof of claim 1, wherein the derivative is 2-acetyl-4-(N-methyl-N-carboxymethylsulfamoyl)-7-n-butoxybenzofuran.

11. The benzofuran derivative or a nontoxic salt thereof of claim 1, wherein the derivative is 2-acetyl-4-[N-methyl-N-(1-carboxyethylsulfamoyl)]-7-n-butoxybenzofuran.

12. The benzofuran derivative or a nontoxic salt thereof of claim 1, wherein the derivative is 2-acetyl-4-[N-(1-carboxyethyl)sulfamoyl)]-7-n-butoxybenzofuran.

13. The benzofuran derivative or a nontoxic salt thereof of claim 1, wherein the derivative is 2-carboxy-4-(N-carboxymethylsulfamoyl)-7-carboxymethoxybenzofuran.

14. The benzofuran derivative or a nontoxic salt thereof of claim 1, wherein the derivative is 2-carboxy-4-(N-carboxymethylsulfamoyl)-7-methoxybenzofuran.

15. The benzofuran derivative or a nontoxic salt thereof of claim 1, wherein the derivative is 2-carboxy-4-(N-carboxymethylsulfamoyl)-7-ethoxybenzofuran.

16. The benzofuran derivative or a nontoxic salt thereof of claim 1, wherein the derivative is 2-acetyl-4-(N-carboxymethylsulfamoyl)-7-methylbenzofuran.

17. The benzofuran derivative or a nontoxic salt thereof of claim 1, wherein the derivative is 2-acetyl-4-(N-carboxymethylsulfamoyl)-7-sec-butylbenzofuran.

18. The benzofuran derivative or a nontoxic salt thereof of claim 1, wherein the derivative is 2-acetyl-4-(N-carboxymethylsulfamoyl)-5,6-methylenedioxybenzofuran.

19. The benzofuran derivative or a nontoxic salt thereof of claim 1, wherein the derivative is 2-acetyl-4-methoxy-7-(N-carboxymethylsulfamoyl)benzofuran.

20. The benzofuran derivative or a nontoxic salt thereof of claim 1, wherein the derivative is 2-(4-methyl-2,5-dioxoimidazolidine-4-yl)-4-(N-carboxymethylsulfamoyl)-7-methoxybenzofuran.

21. The benzofuran derivative or a nontoxic salt thereof of claim 1, wherein the derivative is 2-(4-methyl-2,5-dioxoimidazolidine-4-yl)-4,6-di(N-carboxymethylsulfamoyl)-7-methoxybenzofuran.

22. The benzofuran derivative or a nontoxic salt thereof of claim 1, wherein the derivative is 2-ethyl-3-(N-carboxymethylsulfamoyl)-5-nitrobenzofuran.

23. The benzofuran derivative or a nontoxic salt thereof of claim 1, wherein the derivative is 2-ethyl-3-(N-carboxymethylsulfamoyl)-5-acetylaminobenzofuran.

24. A pharmaceutical composition for treatment of diabetic complications which comrises a benzofuran derivative having the formula (I):

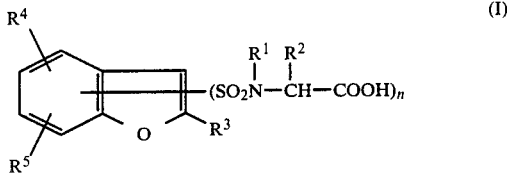

wherein $R^1$ is hydrogen atom, a benzyl group, unsubstituted or substituted with a halogen atom or.an alkyloxy group, or an alkyl group having 1 to 3 carbon atoms, $R^2$ is hydrogen atom or an alkyl group having 1 to 3 carbon atoms, $R^3$ is acetyl group, ethyl group, carboxyl group or 4-methyl-2,5-dioxoimidazolidine-4-yl-group, $R^4$ is hydrogen atom, hydroxyl group, an alkyl group having 1 to 6 carbon atoms, an alkoxy group having 1 to 9 carbon atoms, carboxymethoxy group, nitro group, acetoamino group, a benzyloxy group, unsubstituted or substituted with a halogen atom, nitro group or an alkyloxy group, or a group having the formula: $-OR^6$, wherein $R^6$ is an alkenyl group having 2 to 4 carbon atoms or an alkyl group having 2 to 3 carbon atoms having a halogen atom, cyano group or oxo group, $R^5$ is hydrogen atom or methylenedioxy group together with $R^4$ group, n is 1 or 2, and the unsubstituted or substituted N-carboxymethylsulfamoyl group, $R^4$ and $R^5$ are attached at 3-position, 4-position, 5-position, 6-position or 7-position of the benzofuran ring, or a nontoxic salt thereof, and a pharmaceutically acceptable carrier.

25. A method for treatment of diabetic complications in a diabetic mammal which comprises administering to said mammal an effective amount of a benzofuran derivative according to claim 1.

* * * * *